United States Patent [19]

Nambu et al.

[11] Patent Number: 4,735,207
[45] Date of Patent: Apr. 5, 1988

[54] ELECTRODE FOR USE IN ELECTRORETINOGRAPHY

[75] Inventors: Masao Nambu, Yokohama; Yoshihito Honda, Kyoto; Nobuhisa Naoi, Takarazuka, all of Japan; Si Y. Kim, Taegu, Rep. of Korea; Ei Sakaue, Ehime, Japan

[73] Assignee: Nippon Oil Co., Ltd., Tokyo, Japan

[21] Appl. No.: 836,659

[22] Filed: Mar. 5, 1986

[30] Foreign Application Priority Data

Mar. 7, 1985 [JP] Japan ................... 60-43815

[51] Int. Cl.$^4$ ............................................. A61B 5/04
[52] U.S. Cl. .................................. 128/639; 128/642; 128/793; 128/798
[58] Field of Search ............... 128/639, 642, 784, 793, 128/798

[56] References Cited

U.S. PATENT DOCUMENTS

| | | | |
|---|---|---|---|
| 3,998,215 | 12/1976 | Anderson et al. | 128/641 |
| 4,109,648 | 8/1978 | Larke et al. | 128/639 |
| 4,474,570 | 10/1984 | Ariura et al. | 128/798 |
| 4,617,935 | 10/1986 | Cartmell et al. | 128/641 |

OTHER PUBLICATIONS

Y. Honda, "General Examination Methods in Opthamology" (Opthamologic MOOK (3)), pp. 137 ff. (1978).

J. G. F. Worst et al, *Am. J. Ophth.*, vol. 51, pp. 410 ff. (1961).

H. Kawabata, *Annual Review of Japanese Opth. Soc.*, vol. 18, pp. 848 ff. (1967).

Y. Kubota, *J. Japanese Opth. Soc.*, vol. 67, pp. 185 ff. (1963).

D. Yonemura et al., *Opthamology*, vol. 13, pp. 455 ff. (1971).

*Primary Examiner*—Kyle L. Howell
*Assistant Examiner*—Randy Citrin
*Attorney, Agent, or Firm*—Jordan and Hamburg

[57] ABSTRACT

This invention is directed to an electrode for use in electroretinography. The electrode contains a thin membrane made of a hydrogel of high water content and a conductor connected to the thin membrane. The thin membrane is prepared by casting an aqueous polyvinyl alcohol solution into a mold, freezing the cast aqueous solution to obtain a frozen mass, thawing the frozen mass and subjecting the thawed mass to one to seven additional cyclic freezing and thawing treatments. The thin membrane can also be prepared by subjecting the frozen mass to partial dehydration in a vacuum until the percentage dehydration rate reaches not less than 3 wt %.

16 Claims, 1 Drawing Sheet

ELECTRODE FOR USE IN ELECTRORETINOGRAPHY

BACKGROUND OF THE INVENTION

The present invention relates to a thin film-shaped electrode adapted to contact with a cornea or a conjuctiva bulbi for obtaining an electroretinogram as general information or record concerning the action potentials of stratum retinae induced by stimulus of light irradiation.

It has already been adopted as one of the routine examinations to detect electric potential shift of the retina induced by stimulus of light irradiation to learn the action or exitation of the neuroepitheliale retinae and the stratum ganglionare retinae to utilize the means or supplementing data for diagnosis of oculopathy. In such an examination, it is a common practice to place a conductor (differential electrode) in fornix conjunctivae or on the cornea to detect the potential shift between a reference electrode (indifferent electrode) bonded to the forehead or ear lobe, the thus detected shift in potential being amplified and recorded, in order to measure the potential of the retina which is embedded deeply in the orbita without subjecting the eyeball organisms to any invasion. Such a technique has been disclosed for example, in Yoshihito Honda, "Eye and Electrophysiology (Ophthalmologic MOOK (14))", page 284 (1980), Kanehara Shuppan K.K.; Yoshihito Honda, "General Examination Methods in Ophthalmology (Ophthalmologic MOOK (3))", page 137 (1978), Kanehara Shuppan K.K.; and Isamu Tsukahara and Eli Sakaue "Textbook of Ophthalmology", page 156 and page 168 (1968), Kanehara Shuppan K.K. As the indifferential electrode used in this examination, a silver plate electrode analogous to the electrode used in the electroencephalography may be effectively used with the silver chloride face thereof firmly contacting the skin of the ear lobe or the like.

However, a fully satisfactory differential electrode which is fitted directly on the cornea or conjunctiva has not yet been developed, and research continues to develop an electrode suited for such an application to satisfy the requirement that damage of the eyeball organisms should be minimised. (In this connection, reference should be made to Ryoji Asayama, Makoto Nagata et al., "Jap. J. of Clinical Ophthalmology" vol. 11, 304 (1957) and J. G. F. Worst et al., Am. J. Ophthalmol., vol 51, 410 (1961).) The use of silver foil, silver-plated Nylon string, silver-coated hard contact lens, gold-coated hard contact lens and platinum-coated hard contact lens has been proposed, for example, by Kenji Yanashima et al., "Jap. J. of Clinical Ophthalmology" vol. 37, 777 (1983); Heiichiro Kawabata, "Annual Review of Japanese Ophthalmological Society", vol. 18, 848 (1967); and Yasuo Kubota, "Journal of the Japanese Ophthalmological Society", vol. 67, 1985 (1963) and "Jap. Rev. of Clinical Ophthalmology" vol. 76, 430 (1982). It has also been proposed to use cotton impregnated with physiological saline solution, carbon fibers or a hard contact lens coated with carbon fibers, for example, by Hiroya Sato, "Jap. J. of Clinical Ophthalmology" vol. 25, 743 (1971), and Daizo Yonemura et al., "Ophthalmology", vol 13, 455 (1971). However, all of the prior art means has at least one defect or disadvantage such as the uncomfortable feeling caused by a foreign body, difficulty in firm fitting, irritation or damage of the tissue, drying of the cornea or electrical noises due to the photoelectric effect or Becquerel effect.

On the other hand, it is desirous that a "disposable" differential electrode be developed in order to obviate cross-infection between patients subjected to the examination. However, it is not expected to reduce the production cost of any one of the electrodes described above considerably if they are made disposable since they are produced through complicated production processes. Under such circumstances, it is inevitable that it takes time for sterilizing a differential electrode prior to the repeated use thereof.

It has been tried to use a soft contact lens for such a purpose. However, in addition to the cost problem, the mechanical strength of a soft contact lens is reduced as the water content, i.e. the content of physiological saline solution contained therein, of the material for the soft contact lens is increased to meet the requirement that the conductivity thereof be increased. It has been pointed out that even a soft contact lens for common use containing a relatively small amount of water (ranging from 35% to 55%) is seriously contaminated with bacteria or fungi, thus requirring scrupulous and frequent sterilization, and that a soft contact lens is apt to be broken or damaged during handling operations including sterilization, fitting and detachment, as reported by Yutaka Mizutani, "Contact Lens (Ophthalmologic MOOK (2))", page 45 (1978), Kanehara Shuppan K.K., and by Yoichi Ohta, ibid., page 212. A soft contact lens which is improved in mechanical strength to some extent and contains about 70% of water has been proposed recently. However, the soft contact lens according to this recent proposal is detrimental in frequent daily handling operations including frequent repeated fitting ad detaching operations and scrupulous sterilization operation. Another disadvantage of the soft contact lens according to this recent proposal is that it is relatively expensive since it is produced through a complicated production process involving a spin-casting or a lathe-cut step, which poses a serious barrier to use it as a disposable lens.

With the aim of eliminating direct contact of an electrode with the eyeball tissue, it has been proposed to use a skin electrode which is applied to angulus oculi medialis or the lower eyelid. Such proposals are disclosed by Yoshihito Honda, "Ophthalmology", vol. 17, page 135 (1975); and Y. Honda et al., J. Pediatri. Ophthalmol. Strab., 16, 62 (1979) and 20, 153 (1983). Although many disadvantages of the conventional technology can be solved by adopting the last-mentioned proposal, such means is detrimental in S/N ratio (signal to noise ratio) and inferior in reproducibility of the result of measurement since the electric signal from the eyeball tissue is not detected directly.

SUMMARY OF THE INVENTION

Accordingly, a principal object of this invention is to provide a highly elastic and light-weight electrode for use in electroretinography, which electrode may be fitted easily without uncomfortable feeling due to foreing bodies, does not irritate or inflict damage to the living tissue and keeps the cornea in a well-wetted condition.

Another object of this invention is to provide an electrode for use in electroretinography improved to have a satisfactory fitting property and also improved in conductivity to give precise measuring results with good reproducibility and with remarkably decreased electrical noises.

A further object of this invention is to provide an electrode for use in electroretinography, which has high mechanical strength and yet can be readily cut to have a desired shape and dimensions.

A still further object of this invention is to provide an electrode for use in electroretinography, which is produced through a simple process at a low cost and thus may be used as a disposable electrode.

The above and other objects of this invention will become apparent from the following detailed description thereof.

According to a first important aspect of this invention, there is provided an electrode for use in electroretinography comprising a thin membrane made of a hydrogel having a high water content and a conductor connected to the thin membrane, the thin membrane being prepared by a process comprising a casting step of casting an aqueous solution containing more than 8 wt % and not more than 30 wt % of a polyvinyl alcohol having a degree of hydrolysis of not less than 98 mol % and an average polymerization degree of not less than 1000 into a mold having desired shape and dimensions, a freezing step of cooling the cast aqueous solution to a temperature of not higher than − (minus) 10° C. to obtain a cooled frozen mass, a thawing step of thawing the cooled frozen mass, and one to seven additional cyclic processing steps each including the freezing and thawing steps.

According to a further aspect of this invention there is provided an electrode for use in electroretinography comprising a thin membrane made of a hydrogel having a high water content and a conductor connected to the thin membrane, the thin membrane being prepared by a process comprising a casting step of casting an aqueous solution containing more than 8 wt % and not more than 30 wt % of a polyvinyl alcohol having a degree of hydrolysis of not less than 98 mol % and an average polymerization degree of not less than 1000 into a mold having desired shape and dimensions, a freezing step of cooling the case aqueous solution to a temperature of not higher than − (minus) 10° C. to obtain a cooled frozen mass, and a partial dehydration step of dehydrating the cooled mass of the cast aqueous solution in vacuum until the dehydration rate reaches not less than 3 wt %.

DETAILED DESCRIPTION OF THE PREFERRED EMBODIMENTS

Figure 1:
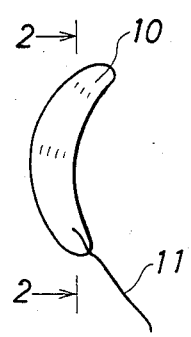
FIG. 1 is a plan view showing an embodiment of the electrode for use in electroretinography, according to the present invention.

The present invention will now be described more in detail.

A thin film or membrane used as the material for the electrode used in the electroretinography is prepared from a hydrogel of high water content through the defined process which will be described in detail hereinbelow.

The polyvinyl alcohol used as the material for the hydrogel in the invention should have a degree of hydrolysis of not less than 98 mol %, preferably not less than 98.5 mol %. It is also essential that the polyvinyl alcohol has an average polymerization degree of not less than 1000.

According to the present invention, an aqueous solution containing the aforementioned polyvinyl alcohol is prepared at initially. The concentration of polyvinyl alcohol in the solution should be within the range of more than 8 wt % and not more than 30 wt %, preferably from 9 to 25 wt %.

In the next step, the aqueous solution of polyvinyl alcohol is cast in a mold for molding a generally flat membrane or for molding an arcuated, hemi-spherical or spheroidal membrane, followed by cooling to a temperature of not higher than − (minus) 10° C., for example from −10° to −80° C., to freeze the same, and then the frozen mass is thawed. The sequential freezing and thawing steps are repeated 2 to 8 times to prepare the rubber-like hydrogel used in the invention. Although the hardness of the hydrogel or rubber-like elastomer is increased as the number of repeated freezing-thawing cycles is inreased, the increment in hardness and strength of the gel becomes smaller with the increase of the repeated cycles and the merit obtainable by an additional cycle is not so great as to add a further processing after the ninth cycle [see Masao Nambu, "Polymer Application", 32, 523 (1983)]. In view of the foregoing, it is economically advisable to process the frozen mass of aqueous polyvinyl alcohol solution for an additional 1 to 7 repeated cycles.

According to an alternative feature of the invention, the frozen mass of aqueous polyvinyl alcohol solution may be partially dehydrated in a vacuum, without being thawed, after it is frozen at a temperature of not higher than − (minus) 10° C., in lieu of subjecting the same to the repeated thawing-freezing cycles. By the dehydration step, the mechanical strength of the gel is improved as the dehydration rate (percentage reduction in weight of the solidified gel by cooling) is raised. However, it is not required to raise the percentage dehydration rate to extremely high extent to form a hard gel, but it is desirous that the percentage dehydration rate is set to the level of not less than 3 wt %, and preferably ranges from 3 wt % to 35 wt %, in order to form a soft gel having satisfactory elasticity or resiliency. The partial dehydration step carried out in a vacuum means that water is removed from the frozen mass in a vacuum to some extent. The pressure at the partial dehydration step is not critical and may be, for example, not more than 1 mm Hg, preferably not more than 0.1 mmHg and more preferably not more than 0.08 mmHg.

The mold used in the casting step is not particularly limited as long as it molds a thin film or membrane having an arcuated contour resembling an ordinary soft contact lens, such as a corneal lens, micro-lens or corneoscleral lens, or a thin film or membrane having a generally flat disk-like shape having a certain diameter suited for such an application. The thickness, uniformity or distribution of the thickness, dimensions, shape and radius of curvature of the cast mass may be selected in consideration of the aimed clinical use. In general, when used as a differential electrode, the membrane may generally have a thickness of from 0.1 to 0.8 mm, preferably from 0.1 to 0.3 mm, in order to facilitate easy handling in fitting and detaching operations, firm fitting on an eyeball tissue such as the cornea, conjunctiva bulbi and conjunctiva palpebrarum, and elimination of uncomfortable feeling due to incorporation of a foreign body. Where the membrane is a generally flat disk adapted to be fitted to the fornix conjunctivae, the disk may be a circular or semi-circular plate having a diameter of from 6 to 14 mm, an elliptical or semi-elliptical plate having a diameter along the major axis of from 6 to 14 mm and a diameter along the minor axis of from 4 to 8 mm, or a rectangular plate of 4 to 10 mm × 3 to 10 mm. Where the membrane is an arcuated disk adapted to be fitted to the cornea (sclerocornea), the radius of curvature may range, for example, from 6.5 to 8.5 mm, and the diameter of the disk may range, for example, from 6 to 20 mm. Although it is most convenient to use a mold for molding an article having desired shape and dimensions, a molded material having dimensions or area larger than the desired final article may be molded and the marginal portions of the molded material may be cut off to form the desired article.

When used as an arcuated disk to be fitted to the cornea or the sclerocornea, the portion of the disk covering the pupil may be removed to form an opening having a diameter of from 1 to 8 mm depending on the degree of expected mydriasis so that the stimulating or irradiating light is not absorbed by the electode material. For such an application, the portion of the disk covering the whole cornea may be cut off to form a large opening, and the disk thus prepared may be used as an electrode to be fitted to the sclerocornea or conjunctiva.

In the present invention, a conductor for transmitting an electric signal captured or received by the hydrogel membrane to an amplifier or a recorder is connected to the hydrogel acting as an electrode. A thin string of silver, copper or gold may be used as the conductor. However, in order to obviate the polarization of a metallic material (to measure the oscillatory potential), and the noise signals generated by the photoelectric effect or Becquerel effect caused by irradiation of intensive light, it is preferred to use wetted cotton or carbon as the conductor and it is the most convenient measure to use a cotton thread having a diameter of from 0.3 to 3 mm or a carbon fiber bundle composed of about 30 to 300 carbon filaments each having a diameter of about 10 microns threaded together to have a bundle diameter of from 0.3 to 3 mm. In order to connect the conductor to the hydrogel, one end of the conductor is placed on a surface of the electrode (molded article) and then the same aqueous polyvinyl alcohol solution used for the preparation of the electrode of the invention is coated over the junction portion, followed by the repeated freezing-thawing cycles or freezing-partial vacuum dehydration. It is, of course, possible to insert a thin string of a conductor in the aqueous polyvinyl alcohol solution cast in the mold, prior to the freezing step, so that a solidified mass embedded with one end of the conductor is prepared. The end of the conductor may be inserted in the half-finished mass of the cast article, after the cast mass has been subjected to the freezing-thawing operation once or twice, to prepare a solidified mass embedded with one end of the conductor.

It is preferred that the portion of the conductor expected to contact the living body is electrically insulated, for example by coating with an insulated varnish, in order to eliminate the possibility that the portion of the conductor contact with the palpebrae or face of the patient under examination cause short-circuiting.

Then, the electrode, namely the electrode connected with a conductor covered with an insulating coating, is immersed in a germicidal solution or liquid germicide, followed by repeated rinsing with a large excess of sterilized water, and subsequently the electrode is immersed in a sterilized physiological saline solution over a period of more than about 10 minutes through sterile operations. Through these operations, bacteria, fungi and yeasts possibly contaminating the interiors and surfaces of the electrode and the conductor are rinsed out and removed, and almost all water occupying 70% to 92% of the volume of the electrode is replaced by the phisiological saline solution simultaneously to increase the conductivity of the electrode remarkably.

Alternatively, the operation of immersing the electrode in the sterilized solution or liquid germicide may be dispensed with, and the final product immersed in the physiological saline solution and sealingly packed in a pouch or bottle may be sterilized by irradiation with γ-rays.

The electrode for use in the electroretinography, according to the invention, may be cut to have desired shape and dimensions at the site where a patient is subjected to the examination, in view of the shape and dimensions of the cornea or sclerocornea and in view of the condition of the portion of the living body, e.g. whether any morbid state is found or not.

The electrode of the invention has higher conductivity as compared with known soft contact lenese (containing 5 to 70 wt %, normally 35 to 55 wt %, of water), since the former is extremely increased in water content (content of physiological saline solution) which ranges from not less than 70 wt %, and generally from 80 to 92 wt %. The uncomfortable feeling caused by fitting of the electrode of the invention is comparable to or less than that of the conventional soft contact lens, and the electrode of the invention may be fitted on the desired position easily without using an eyelid speculum. It can be closely fitted on the desired position and may be fitted by a patient who is in the sitting position. The pain or stress born by the patient is relatively small with satisfactory S/N ratio and reproducibility in repeated measurements.

Notwithstanding the fact that an electrode made of the hydrogel of the invention contains a large amount of water, it has a high compressive strength of not less than 3000 kg/cm$^2$ and a high tensile strength of 20 to 40 kg/cm$^2$, which approximates the mechanical strength of silicone rubber containing no water. Yet, the electrode of the invention has a dynamic modulus of elasticity (E') of $2 \times 10^5$ to $3 \times 10^5$ Pa which shows that the electrode of the invention is enhanced in softness in comparison to silicone rubber having a dynamic modulus of elasticity of $5 \times 10^5$ to $6 \times 10^5$ Pa. The electrode of the invention affords a touch resembling soft tissue, such as smooth muscles of a blood vessel, aorta abdominalis and elastic fibers of a blood vessel. This feature of having analogous properties comparable to soft rubber and resembling soft tissue is an important difference from conventional soft contact lens which are harder, more fragile and more easily broken.

The rubber-like hydrogel used in the invention is translucent and has a color resembling milk, although the reason therefor has not been clarified. Accordingly, by placing an electrode provided with a center opening on the cornea or sclerocornea, irradiating light may be incident directly into the pupil through the opening and the scattered light transmitting the translucent milky membrane around the periphery of the pupil passes through the pupil to reach the retina in an evenly scattered condition. As will be understood from the foregoing, the use of the electrode of the invention provides a further merit, over the conventional electrodes made of soft contact lens materials, in that the whole area of the retina including the portion vicinal to the periphery of the pupil is stimulated substantially uniformly.

The material for the electrode of the invention is prepared, as has been described above, by solely subjecting an aqueous polyvinyl alcohol solution to thermal hysteresis within a low temperature or by subjecting the same to freezing and vacuum dehydratation, and no substances harmful to the living organs, such as acids, alkalis, chemicals or cross-linking agents, are used in the preparation process. Therefore, harmful substances need not be removed from the finished product through expensive and laborious processing, and it may be sterilized merely by immersing, for example, in a sterilizing surfactant solution or an aqueous solution of chlorhexyzine (Hibitane) followed by rinsing with sterile water.

Although the electrode of the invention is high in mechanical strength, as mentioned above, to be durable for frequent daily handling operations, it can be produced at a low cost since it is produced through a relatively simple process. In view of this fact, the electrode of the invention has an adaptability for use as a disposable product from the hygienic standpoint, namely in order to obviate troubles caused by adhesion of eye mucus, cross-infection or contamination with bacteria or fungi.

EXAMPLES OF THE INVENTION

The present invention will be described more specifically with reference to some examples thereof. In the following Examples and Comparative Examples, "%" stands for "% by weight".

EXAMPLE 1

Figure 2:
FIG. 2 is a sectional view taken along the line 2—2 in FIG. 1.

A differential electrode 10 as shown in FIGS. 1 and 2 was produced.

A 20% aqueous solution of a polyvinyl alcohol having an average polymerization degree of 1000 and a degree of hydrolysis of 98.5 mol % was poured into a slit (20 cm×5 cm) defined by a glass plate having a thickness of 0.3 mm. Six carbon fibers each having a diameter of 1 mm and a length of 5 cm were juxtaposed at substantially equal intervals of about 3 cm, with about 5 mm of one end of each fiber being immersed in the poured aqueous solution. The slit containing the poured solution was cooled to − (minus) 30° C. to form a frozen mass which was dehydrated at a reduced pressure of 0.1 mmHg to remove about 7% of the contained water, thereafter the temperature of the dehydrated mass is raised back to room temperature to obtain a generally flat hydrogel membrane containing 79% water. The flat hydrogel membrane was cut such that six differential electrodes 10 each having the dimensions of 5×4 mm and one carbon fiber 11 having one end embedded in the solidified hydrogel were produced. An electrically insulating varnish (silicone resin base) was coated over the carbon fiber so that about a 3 cm extension of the carbon fiber from the end at which the carbon filter was connected to the solidified hydrogel was covered with the insulating coating. After allowing to stand over night, the six differential electrodes were immersed in a sterilizer solution (an aqueous solution of Hibitane) over night, and then immersed in 50 ml of sterile water for rinsing. The hydrogel plates or the differential electrodes 10 were rinsed with sterile water an additional three times. During the sterilizing and rinsing operations, each hydrogel plate absorbed water so that the water contet thereof (79% before those operations) was increased to 80%. After immersing in 50 ml of a sterilized physiological saline solution for 30 minutes under a sterile condition, each of the electrodes was contained in a sterilized glass bottle through sterile operations and then each bottle was sealingly closed.

One of the electrodes 10 was put on a bouillon culture medium to be cultured at 37° C. for 7 days. The result was that no microorganism was found.

A physiological saline solution was dropped over the top face of a stainless steel hemisphere having a radius of curvature (13 mm) imitating that of the sclera of an eyeball, and then one of the electrodes was placed gently thereon. The electric resistance between the fore end of the conductor of the electrode and the bottom or inner face of the stainless steel hemisphere was measured to find that the resistance was 15 k$\Omega$.

Another one of the electrodes was used in electroretinography conducted in accordance with the following procedure. An electrode paste (available from Nippon Koden K.K. under the Trade Designation of "P-10E") was coated on an ear lobe of a patient sitting on a shield seat of a hair placed in a dark room, and the silver chloride face of a silver plate electrode was contacted with the electrode paste to be fixed in situ by a black tape. After administrating drops to the left eye of the patient with an ophthalmic solution (containing an anesthetic for the epithelium anterious corneae and ethylcellulose), one of the electrodes of this Example was fitted in the fornix and the conductor of the electrode was connected to an amplifier (available from Nippon Koden K.K. under the Trade Designation of "AVB-2"). After discharging the excess solution, the patient was allowed to sit for 15 minutes to adapt to the darkness. After ascertaining that no abnormality was found in the fitted electrode, the left eye of the patient was irradiated with a flash light emitted by condenser discharge from a 20 joule xenon discharge tube (available from Toshiba Corporation under the Trade Designation of "FT-106") placed and earthed 25 cm from the cornea to be examined. The time constants of the amplifier were set to 0.3 second (for the a and b waves) and to 0.003 second (for oscillatory potential), and the high freqency characteristic of the amplifier was 3 db attenuation at 1 KHz. Clear $a_1$, $a_2$, b and oscillatory potential waves were observed through a cathode ray oscilloscope (available from Nippon Koden K.K. under the Trade Designation of "DC-7"). The measurements were repeated for 4 days, once every day, to reveal that the reproducibilities of the wave form and the heights of respective crests were acceptable, and that the $a_1$, $a_2$, b and the sum of oscillatory potential along the positive direction and the sum thereof along the downward direction were 0.1±0.01:0.08±0.02, 0.24±0.04:0.15≡0.07: and 0.10±0.04 (mV).

COMPARATIVE EXAMPLE 1

Three commercially available electroretinography electrodes (Samples N, S and K to be applied on the cornea) each being composed of a metal-coated hard contact lens were fitted on the cornea of the same person examined in Example 1 to obtain electroretinograms. The samples K and S encountered some difficulties in the fitting operations, and they were fitted using an eyelid speculum available from Handaya K. K. The samples N and S applied a somewhat oppresive feeling after the fitting thereof and resulted in pain by successive fitting extending over 5 minutes or more. The results of electroretinography conducted while using the sample N varied extensively over four time tests, with the maximum values of a, b and OP (oscillatory potential) reaching double the minimum values to show that the electrode sample N did not fit firmly and had inferior stability.

EXAMPLE 2

Figure 3:
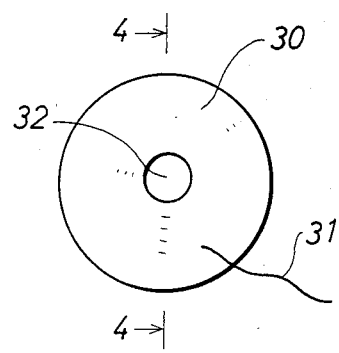
FIG. 3 is a plan view showing another embodiment of the electrode for use in electroretinography, according to the invention.
Figure 4:
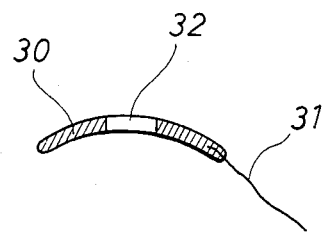
FIG. 4 is a sectional view taken along line 4—4 in FIG. 3.

A differential electrode 30 as shown in FIGS. 3 and 4 was produced.

A 15% aqueous solution of a polyvinyl alcohol having an average polymerization degree of 1200 and a degree of hydrolysis of 99 mol % was cast into a mold for molding an arcuated membrane having a radius of curvature of 8 mm, a uniform thickness of 0.2 mm and a diameter of 13 mm. The thus cast mass was subjected to freezing-thawing steps for two cycles to obtain a half-finished molded mass having a peripheral portion on which one end of a carbon fiber 31 (having a diameter of 1 mm and a length of 5 cm) was placed, the length of the fiber placed on the peripheral portion of the molded mass being 1 cm, and one drop of the same aqueous polyvinyl alcohol solution as used for casting the molded mass was dropped to cover the portion of the fiber engaging the molded mass. Thereafter, the molded mass was subjected to three additional freezing-thawing cycles to obtain a molded product. The center of the molded product was punched off to form an opening 32 having a diameter of 4 mm, and the carbon fiber 31 serving as the conductor was coated with an insulator while leaving a bare fore end of 1 cm in length. The thus obtained hydrogel mass was sterilized, washed with sterile water and packed to produce a differential electrode 30 made of a rubber-like hydrogel containing 85% water. The electrode was fitted on the cornea of the same eye examined in Example 1 and it was subjected to electroretinography similarly as in Example 1 to find that $a_1$, $a_2$, b and the sum of the oscillatory potential waves along the positive direction and the sum thereof along the downward direction were 0.2±0.01:0.15±0.02, 0.45±0.04:0.3±0.07: and 0.2±0.04 (mV). After detaching the aforementioned differential electrode, the cornea was stained with fluorescein and observed through a slit-lamp microscope. The result was that no stained portion was found. The radius of curvature of the cornea of the examined eye was 7.5 mm for the horizontal direction, and 7.7 mm for the vertical direction.

A physiological saline solution was dropped onto a spherical test block attached to the Schioetz tonometer, the differential electrode detached from the examined eye was placed thereon. The electric resistance between the spherical block and the conductor of the electrode was measured to obtain a result of 17 KΩ.

Figure 5:
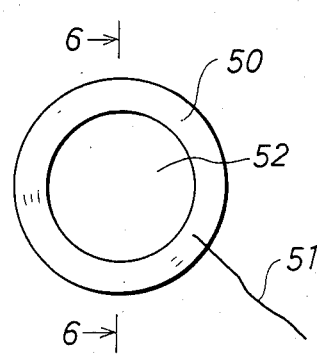
FIG. 5 is a plan view showing a further embodiment of the electrode for use in electroretinography, according to the invention.
Figure 6:
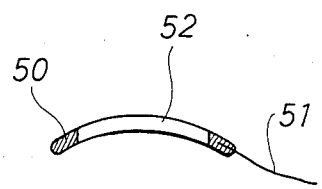
FIG. 6 is a sectional view taken along line 6—6 in FIG. 5.

Although the differential electrode 30 provided with an opening 32 having a relatively small diameter was produced in this Example, a doughnut-shaped differential electrode 50, as shown in FIGS. 5 and 6, provided with an opening 52 of a large diameter may be produced and conveniently used within the scope of the present invention.

COMPARATIVE EXAMPLE 2

The same commercially available electrode samples N and S as used in Comparative Example 1 were fitted in both eyes of the same patient who was examined in Example 1, the electrode samples N and S being detached from the eyes after 3 minutes, and the eyes were stained with fluorescein. The observation of the stained conditions of both eyes revealed that the disorder of epithelium was so serious that about one third of the cornea fitted with the sample N was stained, and that a portion of the cornea fitted with the sample S was stained to show disorder caused thereby in the epithelium.

Althouh the present invention has been described with reference to the specific examples, it should be understood that various modifications and variations can be easily made by those skilled in the art without departing from the spirit of the invention. Accordingly, the foregoing disclosure should be interpreted as illustrative only and not to be interpreted in a limiting sense. The present invention is limited only by the scope of the following claims.

What is claimed is:

1. An electrode for use in electroretinography comprising a thin membrane made of a hydrogel having a thickness from 0.1 to 0.8 mm and a compressive strength of not less than 3000 kg/cm$^2$ and a conductor connected to said thin membrane, said thin membrane being prepared by a process comprising casting an aqueous solution containing more than 8 wt % and not more than 30 wt % of a polyvinyl alcohol having a degree of hydrolysis of not less than 98 mol % and an average polymerization degree of not less than 1000 into a mold having desired shape and dimensions, cooling the cast aqueous solution to a temperature of not higher than minus 10° C. to obtain a cooled frozen mass, thawing said cooled frozen mass, and one to seven additional cyclic processing steps each including said cooling and thawing steps.

2. The electrode as claimed in claim 1, wherein said electrode is shaped as a generally flat membrane.

3. The electrode as claimed in claim 1, wherein said electrode is shaped as an arcuated disk.

4. The electrode as claimed in claim 3, wherein said disk is provided with an opening so that pupil is exposed through said opening when said disk is put on a cornea.

5. The electrode as claimed in claim 1, wherein said conductor is made of a material selected from the group consisting of silver, copper, gold, cotton and carbon.

6. The electrode as claimed in claim 1, wherein a portion of said conductor is adapted to contact a living body and is covered with an electrically insulating material.

7. The electrode as claimed in claim 1, wherein said hydrogel has a water content of not less than 70 wt % and a dynamic modulus of elasticity E' of $2 \times 10^5$ to $3 \times 10^5$ Pa.

8. The electrode as claimed in claim 7, wherein said hydrogel has a water content ranging from 80 to 92 wt %.

9. An electrode for use in electroretinography comprising a thin membrane made of a hydrogel having a thickness of from 0.1 to 0.8 mm and a compressive strength of not less than 3000 kg/cm$^2$ and a conductor connected to said thin membrane, said thin membrane being prepared by a process comprising casting an aqueous solution containing more than 8 wt % and not more than 30 wt % of a polyvinyl alcohol having a degree of hydrolysis of not less than 98 mol % and an average polymerization degree of not less than 1000 into a mold having desired shape and dimensions, cooling the cast aqueous solution to a temperature of not higher than minus 10° C. to obtain a cooled frozen mass, and partially dehydrating the cooled mass of the cast aqueous solution in a vacuum until the percentage dehydration rate reaches not less than 3 wt %.

10. The electrode as claimed in claim 9, wherein said electrode is shaped as a generally flat membrane.

11. The electrode as claimed in claim 9, wherein said electrode is shaped as an arcuated disk.

12. The electrode as claimed in claim 11, wherein said disk is provided with an opening so that a pupil is exposed through said opening when said disk is put on a cornea.

13. The electrode as claimed in claim 9, wherein said conductor is made of a material selected from the group consisting of silver, copper, gold, cotton and carbon.

14. The electrode as claimed in claim 9, wherein a portion of said conductor is adapted to contact a living body and is covered with an electrically insulating material.

15. The electrode as claimed in claim 9 wherein said hydrogel has a water content of not less than 70 wt % and a dynamic modulus of elasticity E' of $2\times10^5$ to $3\times10^5$ Pa.

16. The electrode as claimed in claim 15, wherein said hydrogel has a water content ranging from 80 to 92 wt %.

* * * * *